(12) United States Patent
Li et al.

(10) Patent No.: US 10,188,752 B2
(45) Date of Patent: Jan. 29, 2019

(54) DUAL-MODALITY IMAGING PROBE FOR COMBINED LOCALIZATION AND APOPTOSIS DETECTION OF STEM CELLS

(71) Applicant: The Board of Trustees of the Leland Stanford Junior University, Palo Alto, CA (US)

(72) Inventors: Kai Li, Mountain View, CA (US); Heike E. Daldrup-Link, San Francisco, CA (US); Hossein Nejadnik, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 15/669,634

(22) Filed: Aug. 4, 2017

(65) Prior Publication Data
US 2018/0036435 A1    Feb. 8, 2018

Related U.S. Application Data

(60) Provisional application No. 62/371,011, filed on Aug. 4, 2016.

(51) Int. Cl.
*A61K 49/00* (2006.01)
*A61K 49/08* (2006.01)
*A61K 49/14* (2006.01)

(52) U.S. Cl.
CPC ........ *A61K 49/0045* (2013.01); *A61K 49/005* (2013.01); *A61K 49/0039* (2013.01); *A61K 49/0056* (2013.01); *A61K 49/08* (2013.01); *A61K 49/14* (2013.01)

(58) Field of Classification Search
CPC .............. A61K 49/0045; A61K 49/005; A61K 49/0039; A61K 49/0056; A61K 49/08; A61K 49/14
See application file for complete search history.

(56) References Cited

FOREIGN PATENT DOCUMENTS

WO    WO2015014756    2/2015

*Primary Examiner* — Zohreh A Fay
(74) *Attorney, Agent, or Firm* — Lumen Patent Firm (57) ABSTRACT

A ferumoxytol-based dual-modality imaging probe for long-term stem cell tracking through MRI and early diagnosis of cell apoptosis through simultaneous fluorescence imaging is provided. Specifically, a ferumoxytol-based dual-modality imaging probe is provided with enhanced $T_2^*$ relaxivity for tracking stem cells through magnetic resonance imaging and detecting apoptotic stem cells through fluorescence imaging.

1 Claim, 5 Drawing Sheets
Specification includes a Sequence Listing.

SEQUENCE LISTING

<160> NUMBER OF SEQ ID NOS: 1

<210> SEQ ID NO 1
<211> LENGTH: 8
<212> TYPE: PRT
<213> ORGANISM: Unknown
<220> FEATURE:
<223> OTHER INFORMATION: It is a customized peptide sequence that is
    responsive to the presence of activated caspase-3 expressed in
    apoptotic cells.
<220> FEATURE:
<221> NAME/KEY: Lys-Lys-Lys-Lys-Asp-Glu-Val-Asp-7-amino-4-
    Trifluoromethylcoumarin
<222> LOCATION: (1)..(8)

```
-continued

<400> SEQUENCE: 1

Lys Lys Lys Lys Asp Glu Val Asp
1               5
```

DUAL-MODALITY IMAGING PROBE FOR COMBINED LOCALIZATION AND APOPTOSIS DETECTION OF STEM CELLS

CROSS-REFERENCE TO RELATED APPLICATIONS

This application claims priority from U.S. Provisional Patent Application 62/371,011 filed Aug. 4, 2016, which is incorporated herein by reference.

STATEMENT OF GOVERNMENT SPONSORED SUPPORT

This invention was made with Government support under contract AR054458 awarded by the National Institutes of Health. The Government has certain rights in the invention.

STATEMENT TO SEQUENCE LISTING

The Sequence Listing content information recorded in computer readable form is identical to the written on-paper sequence listing.

FIELD OF THE INVENTION

This invention relates to methods, devices, compositions and systems for stem cell tracking.

BACKGROUND OF THE INVENTION

Stem cell transplants offer the possibility to revolutionize clinical medicine by restoring human health rather than repairing defects with remaining functional or anatomical impairments. However, a major barrier for long-term success of stem cell transplants is our inability to recognize complications of the engraftment process in a timely manner.

To date, a large proportion of transplanted stem cells undergo apoptosis and are cleared from the transplantation site by macrophages. An imaging method that could visualize and monitor stem cell transplants directly, non-invasively, and longitudinally in vivo would greatly enhance our ability to develop successful tissue regeneration techniques. Ferumoxytol (Feraheme, AMAG Pharmaceuticals) is approved for anemia treatment by the U.S. Food and Drug Administration. Recently, it has also been used as a contrast agent for stem cell tracking with magnetic resonance (MR) imaging in various animal models.

Although it has been reported that a rapid disappearance of the ferumoxytol label of stem cell grafts in cartilage defects on serial MR imaging studies correlated with graft failure, it is still challenging to diagnose an apoptosis of the transplanted stem cells at early stage after their transplantation with a "one stop" imaging approach. The present invention advances the art with a "one-stop" imaging approach.

SUMMARY OF THE INVENTION

The present invention provides a ferumoxytol-based dual-modality imaging probe for long-term stem cell tracking through MRI and early diagnosis of cell apoptosis through simultaneous fluorescence imaging. Specifically, this invention pertains to the development of a ferumoxytol-based dual-modality imaging probe with enhanced $T_2^*$ relaxivity for tracking stem cells through magnetic resonance imaging and detecting apoptotic stem cells through fluorescence imaging.

Embodiments of the invention could be used:
To track the transplanted stem cells through MRI.
To monitor the stem cell apoptosis through fluorescence imaging.

Embodiments of the invention have the following advantages:
Existing ferumoxytol is only for tracking transplanted stem cells through MRI and it is not feasible to provide the information of apoptosis of stem cells. For instance, diagnosis of the cell apoptosis through MRI signal change is very vague and further histological analysis are always needed to confirm after a long-period post transplantation. The Feru-AFC NPs according to this invention allows one to feasibly tell the transplanted cells are viable or apoptotic after transplantation from fluorescence imaging without other histological staining procedures.

Existing caspase-3 substrate (e.g., DEVD-AFC peptide) is only for in vitro caspase-3 activity tests using cell lysate. Because it is not cell permeable, it could not be used directly for caspase-3 detection in apoptotic cells. As a consequence, it could not be used in stem cell transplantation studies. Through functionalization of KKKKDEVD-AFC (SEQ ID NO:1) on ferumoxytol, the Feru-AFC NPs could easily label stem cells through simple incubation with cells overnight. The internalized Feru-AFC NPs could effectively deliver KKKKDEVD-AFC (SEQ ID NO:1) into cell cytoplasm to facilitate activated caspase-3 detection in apoptotic cells.

The conjugation efficiency of peptide on ferumoxytol surface through the approach provided in this invention is higher as compared to methods from literature. This could allow researchers to achieve high payload of target biomolecules.

Embodiments of the invention could be varied in certain ways, such as:
The fluorescence dye could be changed to a red-emissive one with higher in vivo detection limit.
The fluorescent dye could be changed to DOTA-Gd(III) to make dual MRI imaging nanoparticles. The caspase-3 could cleave DOTA-Gd(III) and release the small molecules so that the T, signal is lost rapidly after the cells undergo apoptosis.
Cell penetrating peptide could be also attached to the ferumoxytol surface to facilitate living cell internalization without using transfection reagent.

BRIEF DESCRIPTION OF THE DRAWINGS

FIGS. 3A-C show according to an exemplary embodiment of the invention fluorescence images of (FIG. 3A) Feru-AFC NP-labeled apoptotic hMSCs after MMC treatment and (FIG. 3B) Feru-AFC NP-labeled viable hMSCs without MMC treatment. The fluorescence from rhodamine phalloidin was recorded by Cy3 channel and the signal from Feru-AFC probes was collected through DAPI channel under the fluorescence microscopy.

FIGS. 4A-C show according to an exemplary embodiment of the invention (FIG. 4A) $T_2^*$-weighted MR images of ferumoxytol (first row) and Feru-AFC NPs (second row) at various Fe concentrations in aqueous solution.

DETAILED DESCRIPTION

To solve the challenge to diagnose an apoptosis of the transplanted stem cells at early stage after their transplantation with a "one stop" imaging approach, the inventors designed and synthesized a dual-modality imaging probe with both superparamagnetic property and fluorescence "light-up" signature, which would allow simultaneous monitoring of the localization and apoptosis of transplanted stem cells. To afford fluorescence response to ferumoxytol, the inventors used a caspase-3 cleavable peptide (KKKKDEVD-AFC, SEQ ID NO:1) to immobilize on the ferumoxytol surface to render the nanoparticles (NPs) fluorescence responsive signature. The inventors took advantage of the surface carboxyl groups from the polyglucose sorbitol carboxymethylether coating of ferumoxytol through carbodiimide reaction to yield high biomolecule payload, which is superior to the previously developed method for ferumoxytol functionalization. As a result, the design of this dual-modality imaging probe, Feru-AFC NPs, could benefit efficient delivery of the peptide into viable cells while the decoration of peptide coating on the ferumoxytol surface could lead to higher $T_2^*$ relaxivity with the hope to yield higher sensitivity in MRI study. Meanwhile, the concept of such imaging probe allows "one stop" labeling strategy of stem cells before transplantation, which minimizes ex vivo cell manipulation. To the best of the inventors' knowledge, this is the first demonstration on ferumoxytol-based dual-modality imaging probe for simultaneous cell apoptosis detection and stem cell tracking with significantly improved $T_2^*$ relaxivity.

Experimental Section

Materials

Ferumoxytol was a commercial product from AMAG Pharmaceuticals, Inc. KKKKDEVD-AFC peptide (SEQ ID NO:1) was customized by GL Biochem Ltd (Shanghai). Dulbecco's modified Eagle's medium (DMEM), fetal bovine serum (FBS) and penicillin-streptomycin solution were provided by Thermo Fisher Scientific. Mitomycin C (MMC), chloroacetic acid, hydrochloride acid, sodium hydroxide, N-(3-Dimethylaminopropyl)-N'-ethylcarbodiimide hydrochloride (EDAC) and N-hydroxysulfosuccinimide sodium salt (sulfo-NHS) were purchased from Sigma-Aldrich. Dialysis tubing (MWCO 12-14 kD and MWCO 3.5 kD) was a product from Spectrum Laboratories. Amicon Ultra-4 Centrifugal Filter Units with Ultracel-10 membrane (MWCO 10 kD) was obtained from EMD Millipore.

Synthesis of Feru-AFC NPs.

To achieve carboxylation of ferumoxytol, ferumoxytol solution (500 µL, 30 mg/mL) was mixed with sodium hydroxide (3 M) and chloroacetic acid (1 M) in 10 mL of aqueous solution under vigorous stirring overnight at room temperature. The carboxylated ferumoxytol nanoparticles were then purified using MWCO 3.5 kD dialysis tubing against DI water for 2 days.

To further conjugate peptide on the carboxylated ferumoxytol surface, N-(3-dimethylaminopropyl)-N'-ethylcarbodiimide hydrochloride (EDAC, 0.1 mmol) and N-hydroxysulfosuccinimide sodium salt (sulfo-NHS, 0.1 mmol) were added into carboxylated ferumoxytol solution under vigorous stirring for 4 h at room temperature. After centrifugation to remove the excess EDAC and sulfo-NHS, KKKKDEVD-AFC peptides (SEQ ID NO:1) (0.02 mmol) were added to the activated ferumoxytol solution for 2 h at room temperature. The mixture was then purified using Amicon Ultra-4 Centrifugal Filter Unit with Ultracel-10 membrane to eliminate excess peptides. Upon dialysis against DI water using MWCO 12-14 kD dialysis tubing for 2 days, the synthesized Feru-AFC NPs were collected and stored at 4° C. for further use. The iron concentration of Feru-AFC NP stock solution was measured using inductively coupled plasma-mass spectrometry (ICP-MS).

Characterization of Feru-AFC NPs

To determine the sizes and zeta potential values of ferumoxytol and Feru-AFC NPs, the samples in 1×PBS solutions at a Fe concentration of 50 µg/mL were analyzed using a Zetasizer Nano ZS equipment. Each sample was analyzed in triplicate.

To determine the relaxivity of ferumoxytol and Feru-AFC NPs, in vitro MRI studies were conducted on a 3 Tesla MRI Bruker ClinScan using a wrist coil. The transverse relaxation times ($T_2^*$) of ferumoxytol and Feru-AFC NPs in water with various of Fe concentrations (0, 2.5, 5, 10, 20, 40 µg/mL) were measured individually using a spin echo sequence with a repetition time TR of 3500 ms, multiple echo times TE of 20, 40, 60 and 80 ms. The $T_2^*$ relaxivity values ($r_2^*$) was obtained from linear least-squares determination of the slope of $1/T_2^*$ relaxation rate ($s^{-1}$) versus the Fe concentration plot.

In Vitro Detection of Feru-AFC NP-Labeled hMSCs with MM

To determine the internalization of Feru-AFC NPs into living cells, the contents of Fe in hMSCs after incubation with ferumoxytol or Feru-AFC NPs with or without addition of lipofectin as the transfection agent were evaluated by ICP-MS. In brief, ferumoxytol or Feru-AFC NPs were diluted in 100 µL of pure DMEM and lipofectin (100 µL) was also mixed with 100 µL of pure DMEM. After 10 min, the as-prepared ferumoxytol or Feru-AFC NPs solution was mixed with lipofectin solution for 15 minutes, followed by dilution into full DMEM supplemented with 10% of FBS and 1% of penicillin/streptomycin to reach a final Fe concentration of 100 µg/mL. The medium (6 mL) was then added into T175 cell culture flask to incubate with hMSCs for 24 h at 37° C. On the other hand, the control groups were incubated with ferumoxytol or Feru-AFC NPs for 24 h without adding lipofectin. The four groups of cells were washed twice with 1×PBS buffer to remove the free NPs and detached by trypsin. The cell pallet (1 million cells in total) after centrifugation was dissolved in 0.5 mL of 26% hydrochloric acid and diluted in 4.5 mL of MilliQ water for ICP-MS analysis. Each sample was analyzed in triplicate and the Fe content was calculated using a standard curve with ICP-MS standard.

To determine the ability of Feru-AFC NPs as a contrast agent in MRI studies, 4 million of Feru-AFC NP-labeled hMSCs using lipofectin as a transfection agent were collected for MR scanning on a 3 Tesla MRI Bruker ClinScan using a wrist coil. MR images of 3 million of hMSCs without NP treatment were also recorded. Each sample was imaged in triplicate and the average transverse relaxation times ($T_2^*$) were calculated.

Statistical Analysis

Data from different groups were analyzed by student's t-test and differences at the 95% confidence level (P<0.05) were considered to be statistically significant.

Fluorescence Response of Feru-AFC NPs to Caspase-3 in Solution

For a pilot study, the inventors tested the fluorescence response of Feru-AFC NPs in the presence of either caspase-3 extract from apoptotic hMSCs or recombinant human caspase-3.

First, hMSCs were treated with 0.1 mg/mL of MMC solution in DMEM for 1 h at 37° C. The cells were then washed twice with 1×PBS buffer and further cultured in complete DMEM supplemented with 10% of FBS and 1% of penicillin-streptomycin for another 24 h at 37° C. After treated with 1× trypsin, the cell pallet was collected through centrifugation and dispersed in 1× cell lysis buffer (AnaSpec, Inc.). The cell suspension (5 million cells) was placed on a rotating apparatus for 30 min at 4° C., followed by centrifugation at 2500× for 10 min. The supernatant containing activated caspase-3 was then collected and stored at −80° C. for further use. Extract from viable hMSCs without treatment of MMC was also prepared according to the same procedure using cell lysis buffer.

In the fluorescence response experiments using cell extract, 50 μL of Feru-AFC NPs (300 μg/mL of Fe) in assay buffer (AnaSpec, Inc.) was mixed with 50 μL of apoptotic hMSC extract or viable hMSC extract in a well of 96-well plate. The mixtures were incubated at 37° C. for 2 h and the fluorescence spectrum was recorded with 400 nm excitation using a BioTek Microplate Reader. On the other hand, recombinant human caspase-3 was also used to monitor the fluorescence change. Feru-AFC NPs (300 μg/mL of Fe) in assay buffer (50 μL) was mixed with 50 μL of DI water, followed by addition of 0.1 μg of recombinant human caspase-3 (R&D System) for 2 h at 37° C. No recombinant human caspase-3 was added in the control group. The mixtures were incubated at 37° C. for 2 h and the fluorescence spectrum was recorded with 400 nm excitation using a BioTek Microplate Reader.

In Vitro Fluorescence Response of Feru-AFC NPs in Cells hMSCs were seeded in the 8-well chamber slide at 5,000 cells/well and cultured in DMEM supplemented with 10% of FBS and 1% of penicillin/streptomycin at 37° C. Feru-AFC NPs were incubated with hMSCs at a final Fe concentration of 100 μg/mL with lipofectin as a transfection reagent. After 24 h incubation, the cell monolayers were washed twice with 1×PBS buffer to eliminate the excess NPs. DMEM containing 0.1 mg/mL of MMC was then added into the sample well for 1 h and replaced by fresh DMEM. The cell monolayer was washed after another 24 h incubation and fixed using neutral buffered formalin. Upon staining with rhodamine phalloidin for 10 min, the cells were mounted using Fluoromount (Sigma-Aldrich) and imaged under Zeiss fluorescence microscopy. The fluorescence of AFC was recorded by DAPI channel while that of rhodamine phalloidin was collected using a Cy3 channel. The fluorescence imaging of apoptotic cells labeled by Feru-AFC NPs was also investigated using IVIS Spectrum In Vivo Imaging System. Feru-AFC NP-labeled hMSCs were treated by MMC for 1 h and further cultured for 24 h at 37° C. All cells (2 million) were then collected and centrifuged to obtain the cell pallet at the bottom of centrifuge tube. The image was recorded under the IVIS Imaging System with excitation at 430 nm and emission at 500 nm. The Feru-AFC NP-labeled hMSCs without MMC treatment were used as control.

Results and Discussion

Figure 1A:
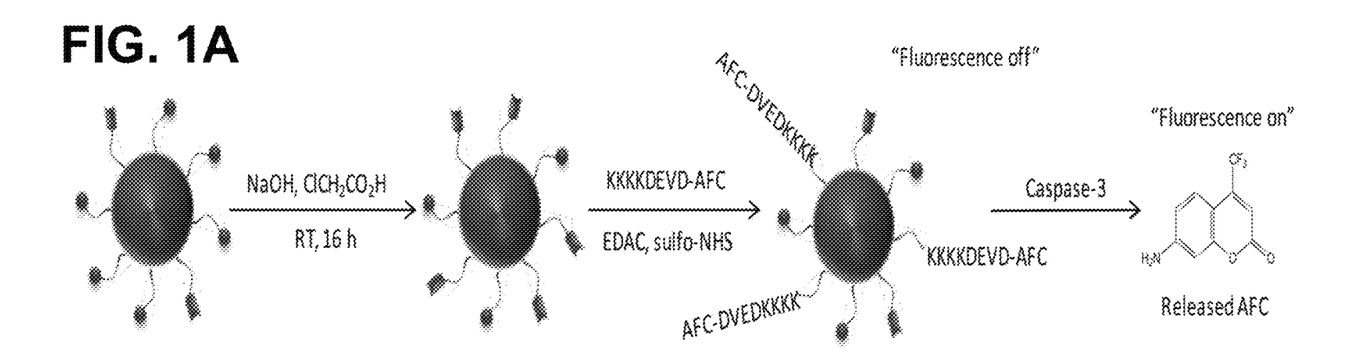
FIGS. 1A-B show according to an exemplary embodiment of the invention in FIG. 1A: Schematic illustration of the synthesis of Feru-AFC, and in FIG. 1B: Size distribution and zeta potential of ferumoxytol and Feru-AFC NPs in 1×PBS buffer, measured by Zetasizer Nano ZS (P<0.05).
Figure 1B:
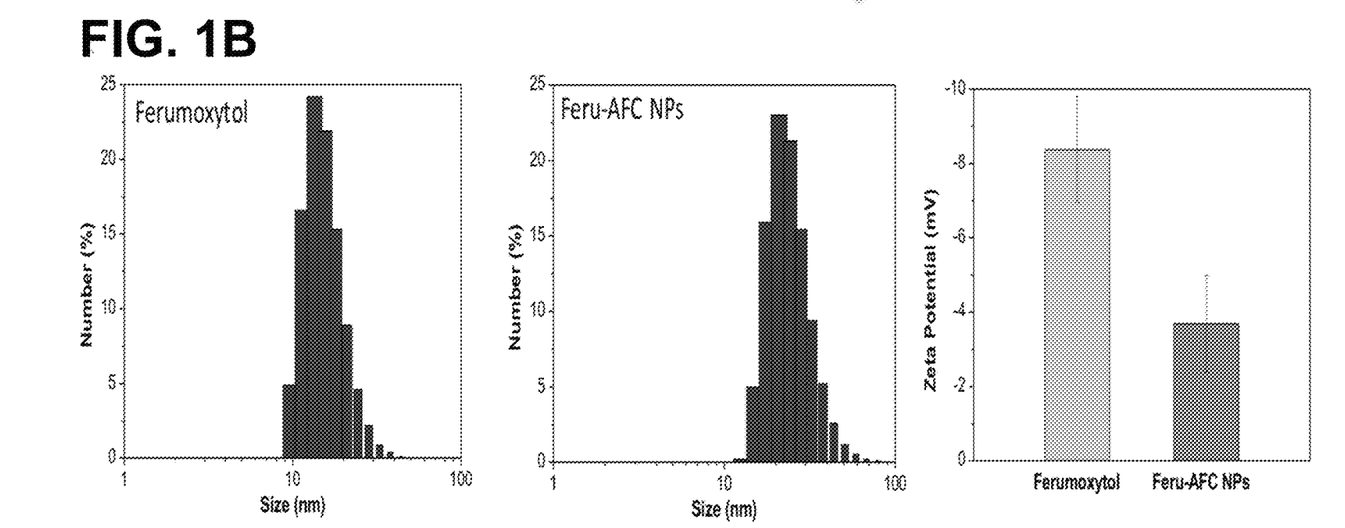

Ferumoxytol was treated with sodium hydroxide and chloroacetic acid for further carboxylation of the hydroxyl groups on surface. The carboxylated ferumoxytol nanoparticles (NPs) were further functionalized with a caspase-3 cleavable peptide, KKKKDEVD-AFC (SEQ ID NO:1), through EDAC-coupling reaction to afford Feru-AFC NPs. The detailed synthetic procedures and mechanism of fluorescence "light-up" in the presence of caspase-3 are shown in FIG. 1a. The average hydrodynamic diameter of obtained Feru-AFC NPs was investigated through a Zetasizer Nano ZS analyzer, which was determined to be 25.33±1.70 nm with a narrow size distribution. Noteworthy is that the average size of Feru-AFC NPs is relatively larger than that of the ferumoxytol NPs without functionalization (16.14±0.98 nm). Additionally, the zeta potential value of Feru-AFC NPs was −8.37±−1.42 mV in 1×PBS buffer, which is less negative as compared to that of ferumoxytol (−3.69±−1.29 mV). These results confirm the successful conjugation of peptides on NP surface. To evaluate the conjugation efficiency of peptide on Feru-AFC NPs, the inventors synthesized gadolinium(III) functionalized ferumoxytol (Feru-Gd) NPs through a similar approach to facilitate the quantification of Gd number on NP surface by ICP-MS. The inventors designed a mimic peptide, KKK-KDEVDC, for immobilization on the surface of carboxylated ferumoxytol NPs through EDAC-coupling reaction. Maleimido-mono-amide-DOTA was further immobilized through thiol-maleimide coupling reaction, followed by chelation of Gd(III) from gadolinium(III) chloride to afford Feru-Gd NPs. After harsh washing steps to eliminate excess Gd(III), ICP-MS results suggest that ~150 Gd(III) are attached on each Feru-Gd NP, indicating the outstanding conjugation efficiency of peptide on ferumoxytol through our approach.

Figure 2A:
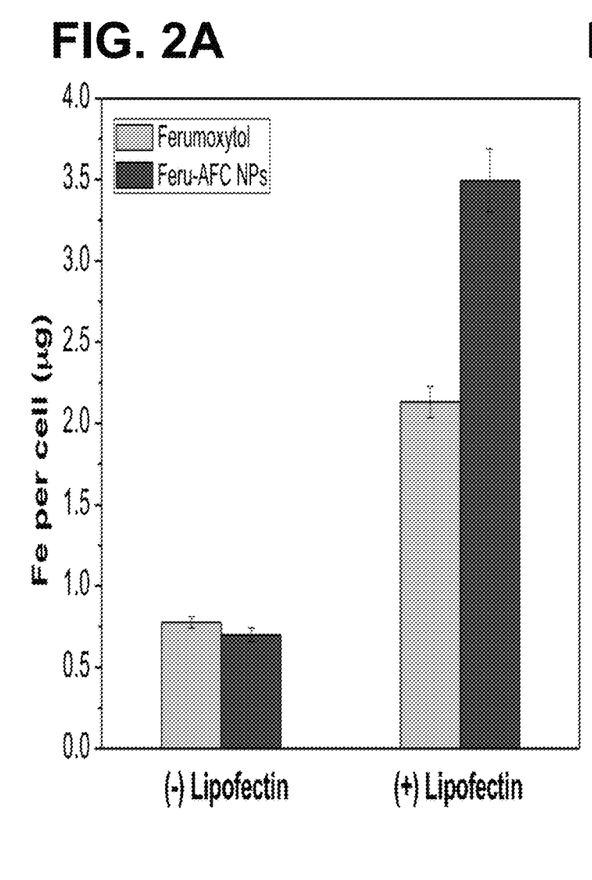
FIGS. 2A-B show according to an exemplary embodiment of the invention in FIG. 2A ICP-MS results of Fe contents in hMSCs after incubation with ferumoxytol or Feru-AFC NPs with/without lipofectin for 24 h at 37° C., and in FIG. 2B fluorescence intensity of Feru-AFC NPs ([Fe]=150 µg/mL) after incubation for 2 h at 37° C. with or without caspase-3 ($\lambda_{ex}$=400 nm). (1) DI water; (2) Feru-AFC NPs in assay buffer; (3) Feru-AFC NPs and recombinant caspase-3 in assay buffer; (4) Feru-AFC NPs and apoptotic hMSC extract with assay buffer; (5) Feru-AFC NPs and viable hMSC extract with assay buffer. The inset shows fluorescence image of solution 1-5 using IVIS Spectrum imaging system ($\lambda_{ex}$=430 nm with the emission at 500 nm).

The uptake efficiency of Feru-AFC NPs in living human mesenchymal stem cells (hMSCs) was further investigated with or without using lipofectin as the transfection reagent. As shown in FIG. 2a, the Fe content in Feru-AFC NP-treated hMSCs is 3.49±0.19 pg per cell using lipofectin as a transfection agent, which is much higher than that in labeled hMSCs without using lipofectin (0.70±0.04 pg per cell). Noteworthy is that the Fe content in ferumoxytol/lipofectin-treated cells is 2.13±0.09 pg per cell, suggesting that the Feru-AFC NPs have higher cell internalization efficiency in the presence of lipofectin. Additionally, the viability of hMSCs after incubation with Feru-AFC NPs at a Fe concentration of 200 μg/mL for 72 h remains above 97%, revealing the low cytotoxicity of Feru-AFC NPs to hMSCs during the test period.

Figure 2B:
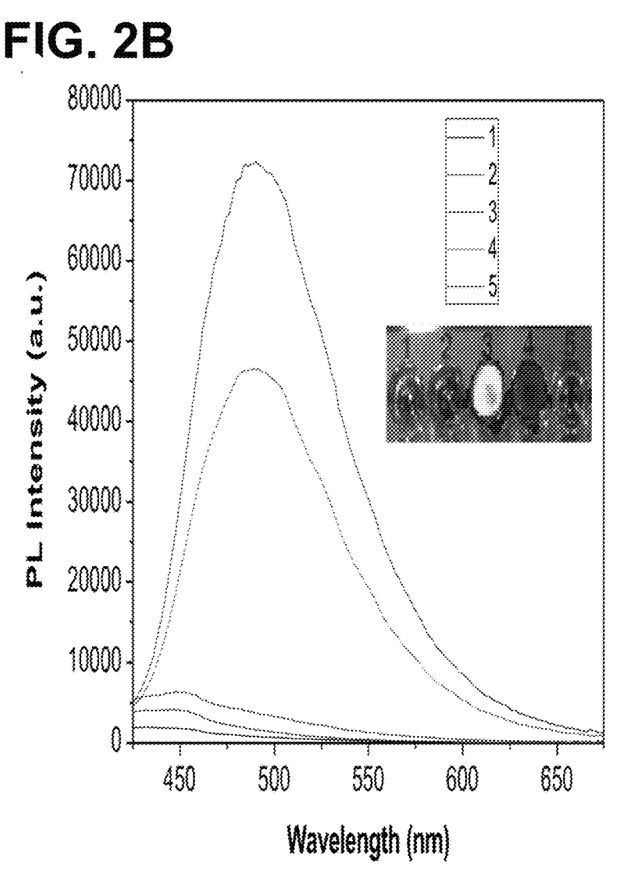

The fluorescence response of Feru-AFC NPs upon exposure to caspase-3 was investigated both in solution and cells. The inventors performed in vitro enzymatic assays using human recombinant caspase-3 first. Feru-AFC NPs were well dispersed in 0.1 mL of caspase-3 assay buffer at a Fe concentration of 150/mL with or without human recombinant caspase-3 (1 μg/mL). After incubation at 37° C. for 2 h, the fluorescence spectra were recorded upon excitation at 400 nm. As shown in FIG. 2b, strong fluorescence signal with a maximum at 495 nm could be observed in Feru-AFC NP solution upon treatment with caspase-3 due to the specific cleavage of DEVD to release AFC fluorophores while no fluorescence could be detected at 495 nm in the absence of caspase-3. To evaluate the fluorescence response of Feru-AFC NPs to activated caspase-3 in cells, the inventors used mitomycin C (MMC) to induce apoptosis of hMSCs to obtain cell lysate containing activated caspase-3. Upon incubation with the apoptotic cell extract, intense fluorescence signal from Feru-AFC NP solution was also observed. On the other hand, the extract from viable hMSCs could not active the fluorescence of probes due to the lack of activated caspase-3, suggesting that the Feru-AFC NPs remain an "off" state in the complex biological environment with great potential to act as a specific light-up probe to activated caspase-3.

Figure 3A:
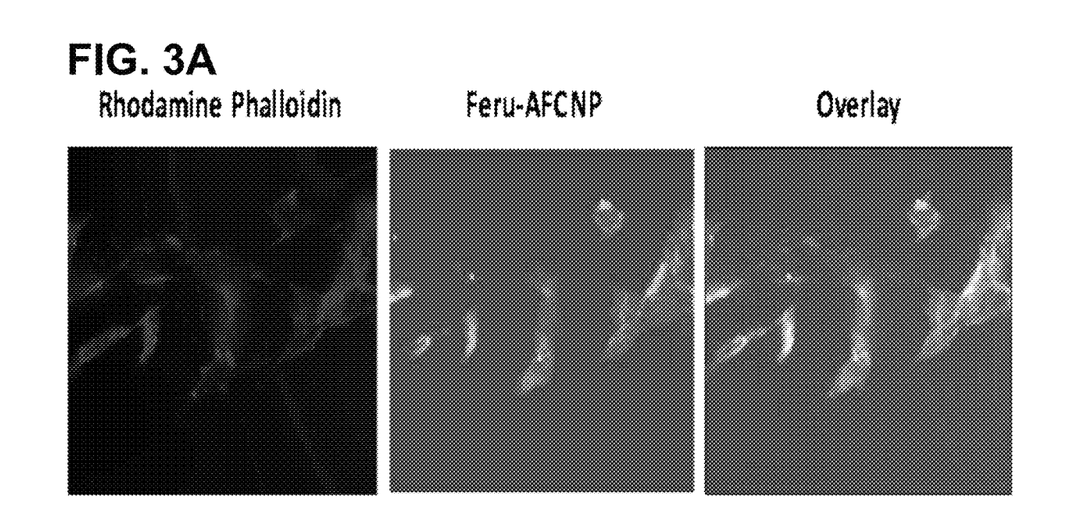
Figure 3B:
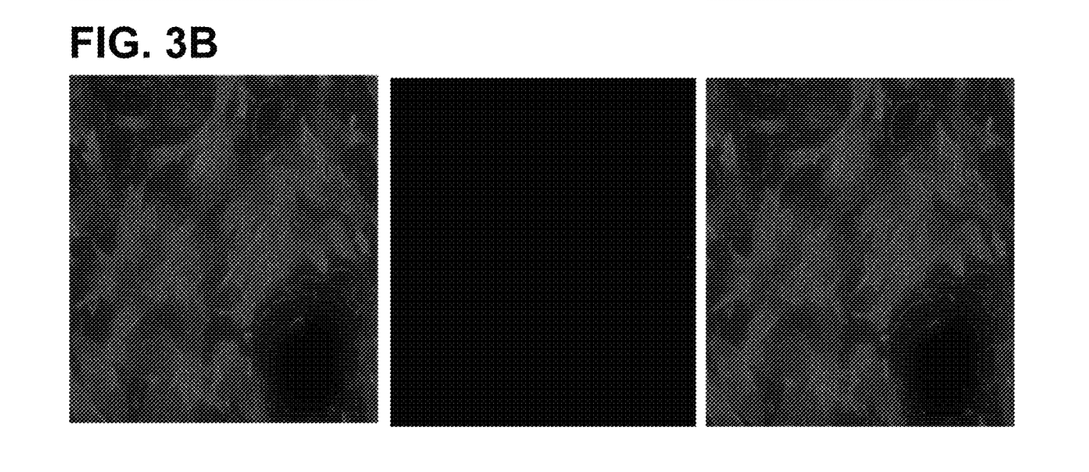
Figure 3C:
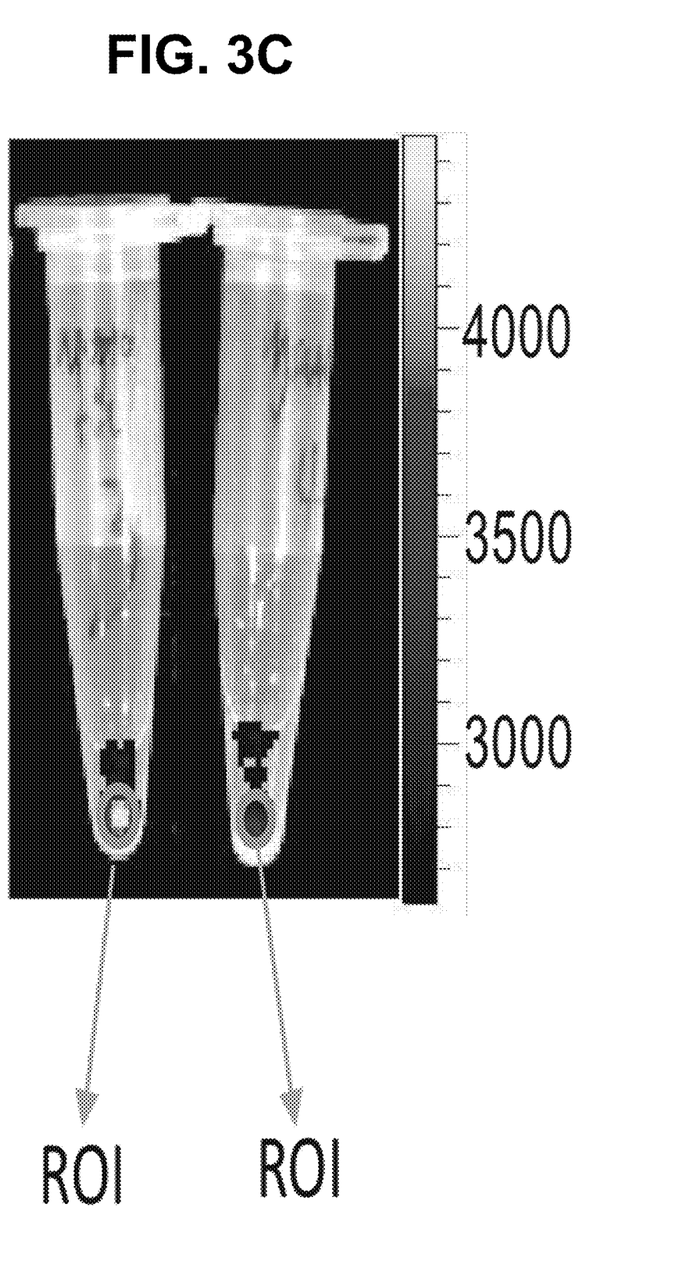
(FIG. 3C) Fluorescence image of Feru-AFC NP-labeled apoptotic hMSCs (left) and viable hMSCs (right), obtained using IVIS Spectrum Imaging System with excitation at 430 nm and emission at 500 nm.

The fluorescence response of Feru-AFC NPs in cells was further investigated. Feru-AFC NPs were first transfected into living hMSCs by lipofectin for 24 h at 37° C. Two groups of Feru-AFC NP-labeled hMSCs were prepared with or without treatment by MMC (0.1 mg/mL) for 1 h, respectively. After 24 h post MMC treatment, the cells were stained by rhodamine phalloidin to visualize F-actin after fixation. As shown in FIG. 3a, clear fluorescence signal from cleaved AFC fluorogens could be observed from MMC-treated hMSCs using DAPI channel under fluorescence microscope. On the contrary, no fluorescence from hMSCs without MMC treatment could be observed under the DAPI channel because the Feru-AFC NPs are able to remain intact in the absence of activated caspase-3 in non-apoptotic cells (FIG. 3b). Additionally, the fluorescence image of apoptotic hMSCs and viable hMSCs was recorded using IVIS Spectrum Imaging System. As shown in FIG. 3c, the fluorescence intensity of region of interest (ROI) from apoptotic cell pellet is twice as high as that from viable cell pellet. These results confirm that the Feru-AFC NPs are promising as sensitive fluorescence "light-up" probe for caspase-3 to indicate cell apoptosis.

Figure 4A:
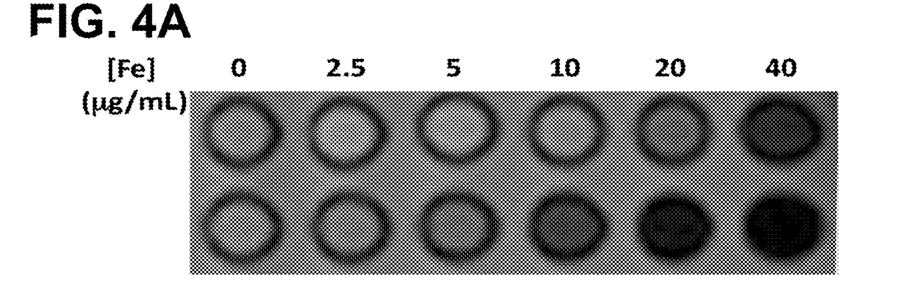
Figure 4B:
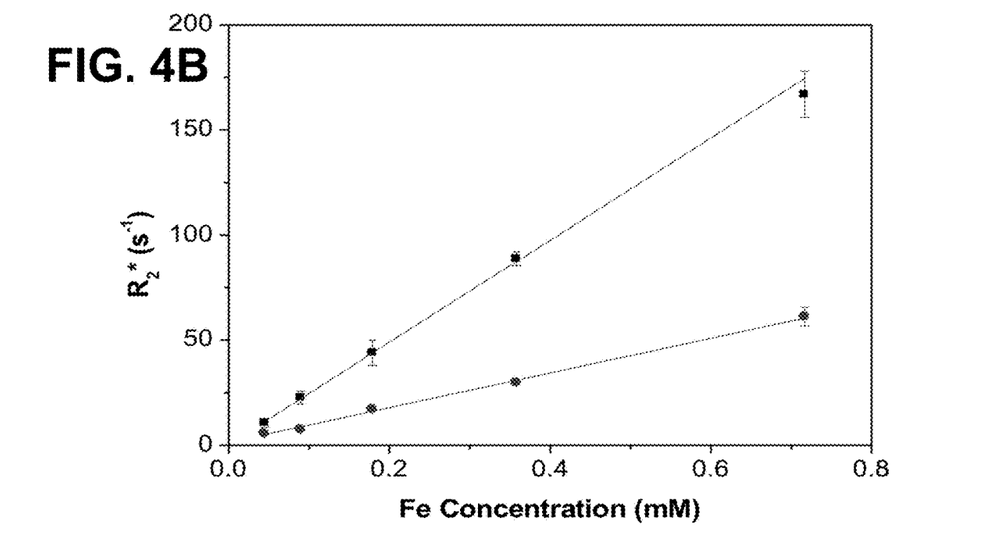
(FIG. 4B) $T_2^*$ relaxation rate ($1/T_2$) of ferumoxytol and Feru-AFC NPs vs. Fe concentration in aqueous solution (n=3, P<0.0001).
Figure 4C:
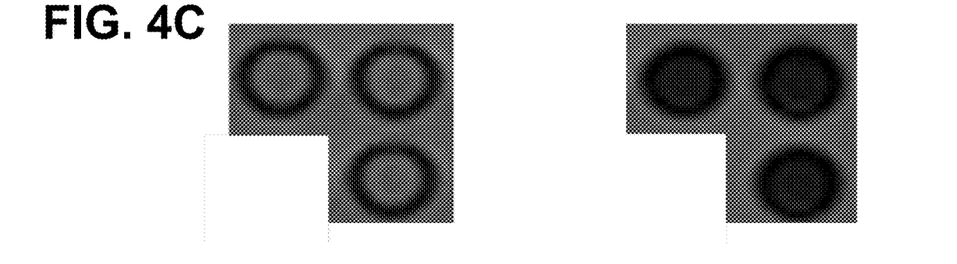
(FIG. 4C) $T_2^*$-weighted MR images of hMSCs (left) and Feru-AFC NP-labeled hMSCs (right).

The transverse relaxation times ($T_2^*$) of the Feru-AFC NPs were investigated using a 3.0-T clinical MRI instrument to demonstrate their utility in practice. FIG. 4a shows the $T_2$-weighted MR image of NP aqueous suspensions at different Fe concentrations. The signal intensity of MR image decreases with increased Fe concentration, indicating that the NPs are able to shorten the transverse relaxation time. The net effectiveness is expressed as $T_2^*$ relaxivity ($r_2^*$), which represents the reciprocal of the relaxation time per unit concentration. As shown in FIG. 4b, the Feru-AFC NPs have a $r_2^*$ value of 242.95±15.12 $mM^{-1}$ $s^{-1}$, suggesting its excellent ability in MRI application. Noteworthy is that the $T_2^*$ relaxivity of Feru-AFC NPs is ~3 times as high as that of ferumoxytol without functionalization (82.29±5.78 $mM^{-1}$ $s^{-1}$). This could be attributed to the attachment of peptide on NP surface that forms a hydrophilic peptide layer, which restricts fast water diffusion and promotes fast proton exchange with water molecules due to abundant surface amides. As such, the water diffusion correlation time is enhanced, leading to an increase of $r_2^*$. The in vitro imaging potential of Feru-AFC NPs was further examined by testing the contrast effect in hMSCs. The MR image of hMSCs after incubation with Feru-AFC NPs shows significantly enhanced contrast compared to that of the non-labeled hMSCs (FIG. 4c), due to the significantly shortened transverse relaxation time of cells after Feru-AFC NP labeling to produce negative contrast in MRI.

In conclusion, the inventors designed and synthesized a dual-modality imaging probe with both superparamagnetic property and fluorescence "light-up" signature, which would allow simultaneous monitoring of the localization and apoptosis of transplanted stem cells. At first, caspase-3 cleavable peptides (KKKKDEVD-AFC, SEQ ID NO:1)) were immobilized on the surface of ferumoxytol nanoparticles with high peptide payload to afford Feru-AFC NPs with higher $T_2$-relaxivity over pure ferumoxytol. The obtained Feru-AFC NPs could be easily internalized into living hMSCs in the presence of lipofectin, as confirmed by ICP-MS results, resulting in a significantly higher $T_2$-weighted contrast compared to unlabeled cells. In the presence of recombinant human caspase-3 or extract of apoptotic hMSCs, Feru-AFC NPs showed intense green fluorescence with a maximum at 495 nm due to specific cleavage of DEVD and release of AFC fluorophores. Accordingly, viable Feru-AFC labeled hMSCs showed no detectable fluorescence, while apoptotic Feru-AFC labeled hMSCs demonstrated intense fluorescence signal under fluorescence microscopy. As such, Feru-AFC NPs represent a novel tool for long-term stem cell tracking through MRI and early diagnosis of cell apoptosis through simultaneous fluorescence imaging after transplantation.

What is claimed is:

1. A dual-modality imaging probe for simultaneous, one-stop, cell apoptosis detection and stem cell tracking, comprising: ferumoxytol with a fluorescent signature peptide immobilized on the surface of the ferumoxytol, wherein the fluorescent signature peptide is a KKKKDEVD-AFC peptide (SEQ ID NO:1).

* * * * *